(12) United States Patent
Martena et al.

(10) Patent No.: US 12,376,825 B2
(45) Date of Patent: Aug. 5, 2025

(54) DEVICE FOR THE DIRECT DETECTION OF PRESSURE VARIATIONS OF A FLUID IN A BODY CAVITY

(71) Applicant: ELECTRONIC SYSTEMS S.P.A., Novara (IT)

(72) Inventors: Florinda Martena, Novara (IT); Stefano Trizzino, Novara (IT)

(73) Assignee: ELECTRONIC SYSTEMS S.P.A., Novara (IT)

( * ) Notice: Subject to any disclaimer, the term of this patent is extended or adjusted under 35 U.S.C. 154(b) by 475 days.

(21) Appl. No.: 17/666,799

(22) Filed: Feb. 8, 2022

(65) Prior Publication Data

US 2022/0249053 A1 Aug. 11, 2022

(30) Foreign Application Priority Data

Feb. 8, 2021 (EP) .................................... 21425003

(51) Int. Cl.
*A61B 8/12* (2006.01)
*A61B 18/14* (2006.01)

(52) U.S. Cl.
CPC ............ *A61B 8/12* (2013.01); *A61B 18/1477* (2013.01); *A61B 2018/1425* (2013.01)

(58) Field of Classification Search
CPC .. A61M 2205/3344; A61M 2205/3331; A61B 5/021; A61B 1/015; A61B 17/3421; A61B 18/1477; A61B 2018/1425; A61B 8/12
See application file for complete search history.

(56) References Cited

U.S. PATENT DOCUMENTS

| | | | |
|---|---|---|---|
| 4,127,110 A | 11/1978 | Bullara | |
| 4,672,974 A | 6/1987 | Lee | |
| 4,966,161 A | 10/1990 | Wallace et al. | |
| 5,312,354 A | 5/1994 | Allen et al. | |
| 6,673,022 B1 | 1/2004 | Bobo et al. | |
| 2006/0276802 A1* | 12/2006 | Vresilovic | A61F 2/4657 623/908 |
| 2007/0016391 A1 | 1/2007 | Minoguchi et al. | |
| 2007/0293786 A1* | 12/2007 | Wekell | A61B 5/0215 600/561 |
| 2013/0053759 A1* | 2/2013 | McCawley | A61B 17/320783 604/22 |
| 2016/0228107 A1* | 8/2016 | Madsen | A61B 17/0469 |
| 2021/0059654 A1* | 3/2021 | Ryan | A61L 24/0031 |

FOREIGN PATENT DOCUMENTS

CN 211749569 U 10/2020

OTHER PUBLICATIONS

Extended European Search Report, EP App. 21425003.7, mailed Aug. 26, 2021 (8 pages).

* cited by examiner

*Primary Examiner* — Gerald Johnson (57) ABSTRACT

A device for the direct detection of pressure variations of a fluid within a body cavity comprises a pressure transducer and a cannula having a distal end which either forms or is fluidically coupled with hollow insertion means suitable to be inserted into the body cavity. The cannula and the hollow insertion means form a volume which contains an air column which can be compressed or decompressed by a pressure variation of the fluid inside the body cavity, the pressure variation of the air column being suitable to cause mechanical deformation of the sensing surface.

12 Claims, 6 Drawing Sheets

DEVICE FOR THE DIRECT DETECTION OF PRESSURE VARIATIONS OF A FLUID IN A BODY CAVITY

The present invention relates to the field of minimally invasive surgical procedures and in particular relates to a detection device capable of directly measuring pressure variations of a fluid within a body cavity, in particular for eye surgery procedures.

Possible fields of application of the device according to the invention are, for example, eye surgical procedures, minimally invasive surgical procedures for the abdomen, e.g. laparoscopic, or for the spinal column, in which it is either necessary or appropriate to measure the cerebrospinal fluid pressure.

For example, substantial pressure variations can occur in the treated eye during eye surgical procedures involving eyeball manipulation, fluid infusion, fragmentation, and aspiration of ocular tissues. Clinical studies have shown that in vitrectomy surgical procedures for vitreous body removal, intraocular pressure can vary between 0 and 120 mmHg. Pressure values above 60 mmHg, which corresponds to retinal perfusion pressure, have been reported in phacoemulsification surgical procedures for cataract fragmentation and aspiration. Large pressure variations have also been measured following eyeball manipulation maneuvers in scleral indentation surgical procedures for the treatment of retinal detachment, with peaks of up to 210 mmHg in the case of external pressures applied to the sclera.

The variations in intraocular pressure can increase the risk of intraoperative and postoperative complications, such as expulsive hemorrhage, choroid detachment, and retinal ischemia. Expulsive hemorrhage and choroid detachment can be associated with pressure drops during surgery. Prolonged increases in intraocular pressure, on the other hand, can result in a reduction in vascular perfusion pressure with consequent impairment of blood flow to the optic nerve and retina. Pressure variations can also adversely affect visual function recovery after the surgical procedure. Indeed, it has been shown that transient increases in ocular perfusion pressure can lead to morphological and functional alterations in the retina. The effects of variations in intraocular pressure on visual acuity can be particularly detrimental to patients with impaired ocular perfusion, e.g. caused by diabetic retinopathy.

Several devices and methods for measuring intraocular pressure have been suggested.

U.S. Pat. No. 4,841,984 describes a device which relies on direct measurement of intraocular pressure using a pressure transducer integrated on the surgical instrument inserted into the ocular cavity, which is used for fluid infusion or fragmentation and removal of ocular tissue. A control circuit is also present which automatically adjusts the infusion or aspiration of the instrument in response to the measured intraocular pressure, keeping it within the safe range. A first limitation of such a device is the need for a larger ocular incision for the insertion of the instrument and the integrated transducer. A further disadvantage is the proximity of the transducer to the surgical instrument, the operations of which inevitably lead to disturbances and inaccuracies in intraocular pressure measurement.

US 20110118729 A1 describes a vitrectome coupled to a control circuit for the purpose of enabling or disabling the instrument based on the measured physical parameter. These parameters can include intraocular pressure, which is used to check whether the vitrectome is positioned correctly within the eye socket. Indeed, to activate the vitrectome, the measured pressure must be equal to the fluid infusion pressure but there is no control over pressure variations relative to the set pressure.

US 20140171991 A1 describes a vitrectome equipped instead with a pressure transducer to monitor the output pressure of the cutting instrument, but no direct monitoring of intraocular pressure is performed.

US 2014194834 A1 describes a device for controlling the pressure in the eye consisting four elements: a positioning cannula (housed in the anterior chamber of the eye), a two-way pump (infusion/aspiration), a control circuit and a pressure sensor housed in the pump reservoir to measure the pressure of the fluid in the reservoir. This device is thus equipped with an indirect measurement system, which allows the measurement of intraocular pressure only in presence of infusion or aspiration of fluid. This system does not allow the measurement of pressure variations caused by external factors or eyeball manipulation.

US 2006/149194 describes a system for treating eye diseases comprising a micro-cannula in which an internal element, configured to exit the distal end of the micro-cannula, can be slidably inserted. The internal element can be used to carry fluids or sensors.

US 2008/0082078 A1 describes a surgical assembly for treating glaucoma comprising a laser configured to produce an ablation beam of a region of a trabecular meshwork of the eye and a delivery system configured to direct the laser beam from within the eye to the trabecular meshwork of the eye, wherein the delivery system can include pressure detection circuitry to detect and control pressure at the surgical site.

WO2016139587A1 describes a surgical assembly for ophthalmic surgical procedures, comprising an optical fiber pressure transducer coupled to a surgical accessory, such as an endoilluminator or infusion cannula, to be jointly inserted into the ocular cavity through an ocular accessory incision.

The monitoring of the pressure variations of a fluid during a surgical procedure is thus of fundamental importance to ensure the safety and effectiveness of the surgical procedure.

It is the object of the present invention to suggest a device which makes it possible to reliably and rapidly detect the pressure variations of a fluid, without suffering from the drawbacks complained above about known devices.

It is another object of the invention to suggest a device for the direct detection of the pressure of a fluid, which is immune from the disturbances associated with the environmental conditions in which the measurement is made.

It is a further object of the invention to limit the number of incisions and to minimize the size of the incisions, to make direct pressure detection less invasive and more tolerable for the patient.

Said objects are achieved with a device for the detection of variations in pressure of a fluid in a body cavity according to claim 1 or according to claim 6, with an assembly according to claim 11 and with a calibration method according to claim 12. The dependent claims describe preferred embodiments of the invention.

The features and advantages of the invention will be apparent from the following description which illustrates preferred embodiments, given by way of indicative, non-limiting examples, with reference to the accompanying figures, in which.

In the following description, two possible embodiments of the invention are illustrated, respectively suitable, for example, for eye surgical procedures and for laparoscopic surgical procedures.

However, it is apparent that the suggested technical teaching can be applied, with possible adaptations, to other types of minimally invasive surgical procedures on the human or animal body.

In the following description, elements common to the different embodiments will be indicated by the same reference numerals.

Figure 1:
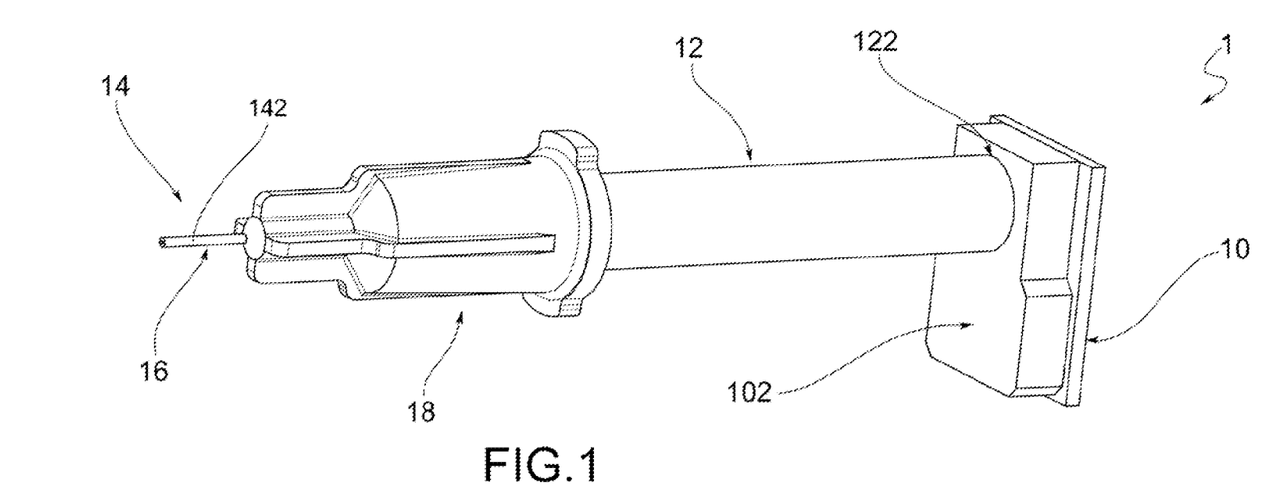
FIG. 1 is a perspective view of the detection device according to the invention, in an embodiment, e.g. suitable for eye surgical procedures.
Figure 2:
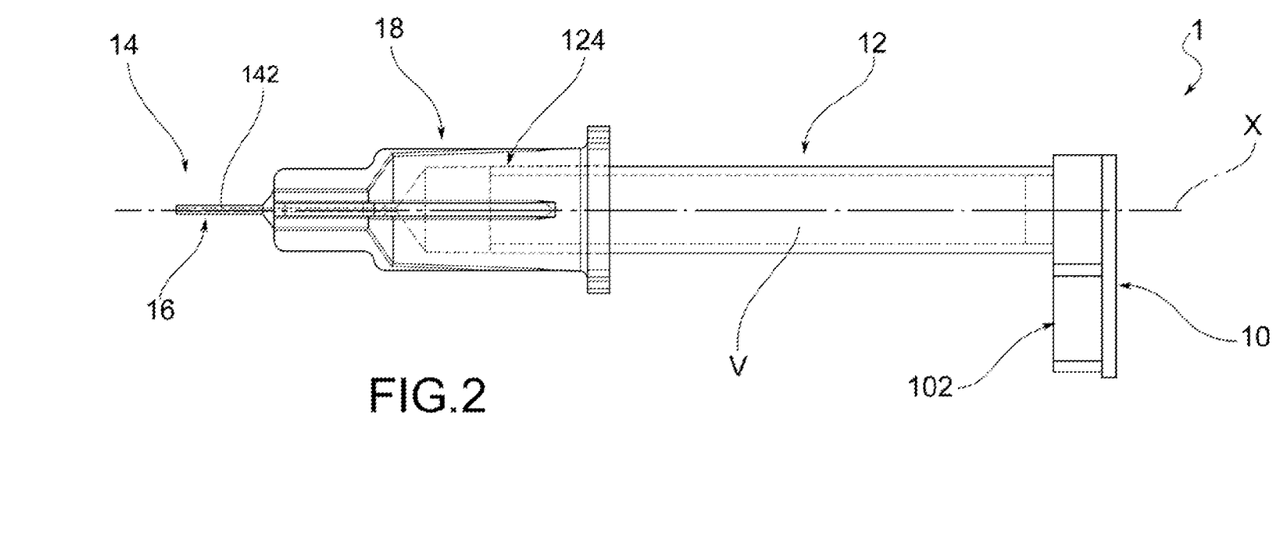
FIG. 2 is an axial section of the device in FIG. 2.
Figure 3:
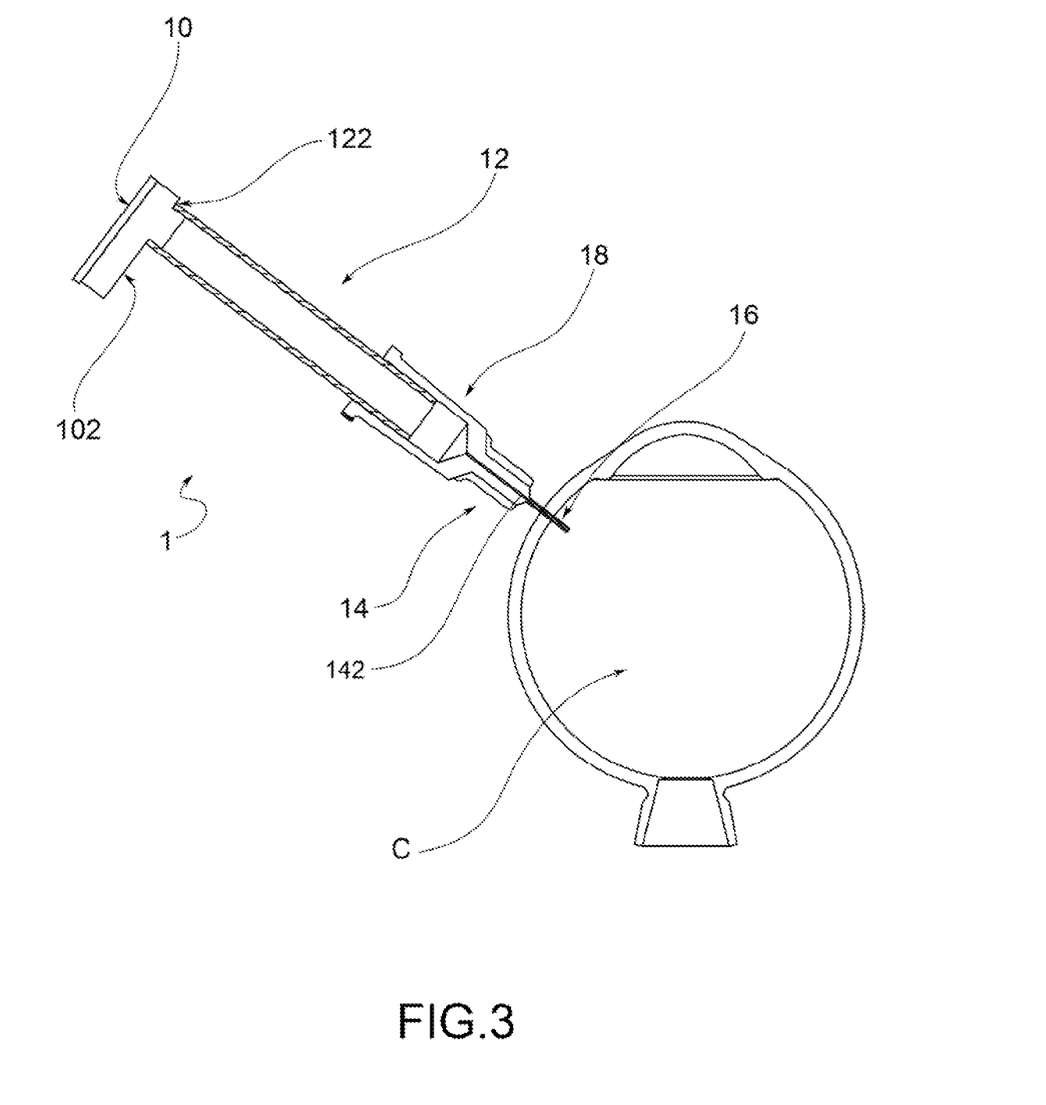
FIG. 3 shows the device in FIGS. 1 and 2 with the needle inserted into the eye socket.
Figure 4:
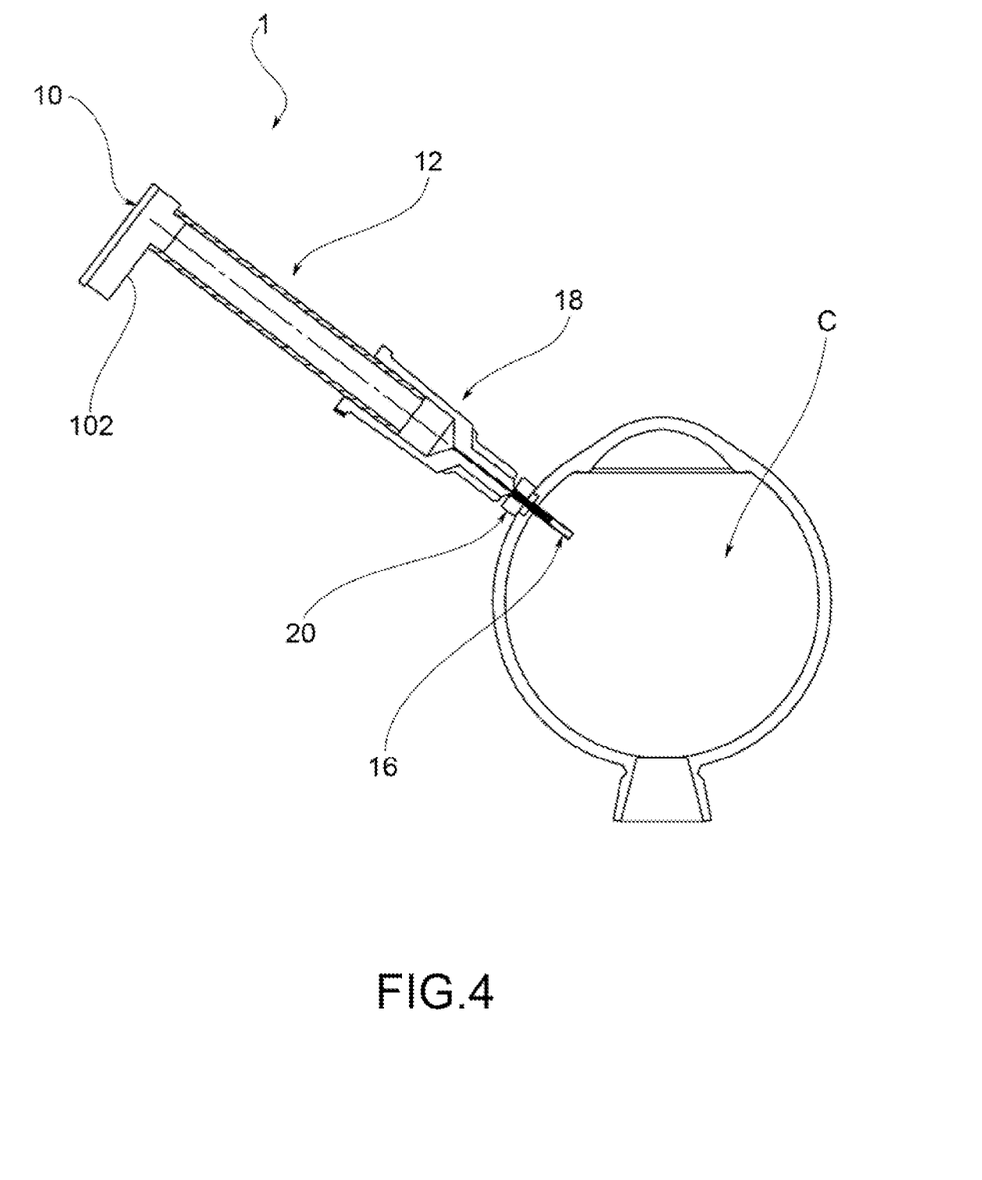
FIG. 4 is a view similar to the previous one, but with the detection device in a variant embodiment.

With reference to FIGS. 1-4, reference numeral 1 refers as a whole to a device for the direct detection of pressure variations of a fluid in a first embodiment, e.g. suitable for use during intraocular surgical procedures (as illustrated in FIGS. 3 and 4) or lumbar surgical procedures.

The device 1 comprises a pressure transducer having a sensing surface 102 suitable to mechanically deform by effect of a pressure acting on it and generate an electrical voltage difference proportional to the mechanical deformation.

In an embodiment, the pressure transducer 10 is a piezoelectric transducer. In this case, the sensing surface 102 is the surface of the piezoelectric material which generates an electrical voltage difference in response to its mechanical deformation.

The detection device 1 further comprises a cannula 12 which extends along a cannula axis X between a proximal end 122 and a distal end 124.

The proximal end 122 is placed in direct contact with the sensing surface 102 of the pressure transducer 10.

The distal end 124 either forms or is fluidically coupled to hollow insertion means 14 suitable to be inserted into a body cavity, e.g. the eye socket C.

In an embodiment, the hollow insertion means 14 comprise a needle 142 suitable to pierce the tissues to access the body cavity.

The principle of operation of the detection device 1 is based on the fact that the cannula 12 and the hollow insertion means 14 form a volume V containing an air column (or possibly another gas or gas mixture) which is either compressible or decompressible due to a variation in intracavitary pressure. The pressure variation of the air column is suitable to cause mechanical deformation of the sensing surface 102 of the pressure transducer.

In other words, the cannula 12 is a tubular element which is open at both ends, on the one hand directly to the sensing surface 102 of the pressure transducer and on the other hand to the hollow insertion means 14, which form a port which puts the cannula 12 into communication with the inside of the body cavity.

Therefore, as shown in FIGS. 3 and 4, the pressure transducer 10 and the cannula 12 are located externally to the body and it is only the needle 142 which is inserted into the cavity.

Therefore, it is not necessary to insert any device inside the organ undergoing surgery.

For example, the cannula 12 has a rigid or semi-rigid body tightly coupled to the pressure transducer 10. The cannula 12 can be a gripping element of the detection device 1 during use.

The mechanical coupling between the cannula 12 and the pressure transducer 10 can be made such that the cannula 12 itself also serves as a support for the pressure transducer 10.

Therefore, the detection device 1 can be formed only of the pressure transducer 10 and the cannula-needle assembly and be connected to a control apparatus 40 only by electrical wires 4.

Therefore, the detection device 1 can be extremely light and easy to handle.

In an embodiment, the distal end 124 of the cannula 12 is coupled to a blunt needle 16.

In an embodiment, the distal end 124 of the cannula 12 is connected to the needle 142; 16 by means of a Luer lock type connector 18.

In an embodiment shown in FIG. 4, the needle 142; 16 is inserted into a guiding cannula 20 of a trocar.

In some embodiments, the distal end of the cannula is coupled with a trocar connector, suitable for connecting to a trocar guide. The hollow insertion means is thus formed by a trocar guide, without the sharp tip, tightly coupled to the trocar connector.

In this case, during the surgical procedure, the trocar guide provided with the sharp tip (also known by the technical term "trocar," although sometimes this term is used to refer to the guide-tip assembly as a whole) is inserted into the body cavity, specifically the posterior chamber, or vitreous, of the eye, through an incision made by the sharp tip of the trocar. The sharp tip is then slipped off the trocar guide. The latter has a proximal connecting end which remains outside the body cavity to be tightly coupled to the trocar connector with which the distal end of the cannula is provided.

Therefore, in use, the needle 142; 16 or trocar guide is adapted to be positioned through the tissue or membrane which delimits the body cavity, so that the distal end of the needle or trocar guide remains within the cavity, while the proximal end of the needle or trocar guide, coupled to the cannula, remains outside the body cavity.

In an embodiment, the piezoelectric transducer 10 has a sensing surface 102 which extends predominantly on a plane substantially orthogonal to the cannula axis (X). In this manner, the pressure variation of the air column within the volume V generates a strain on the sensing surface 102 with a prevailing component orthogonal to the sensing surface 102, maximizing the mechanical deformation thereof.

Figure 5:
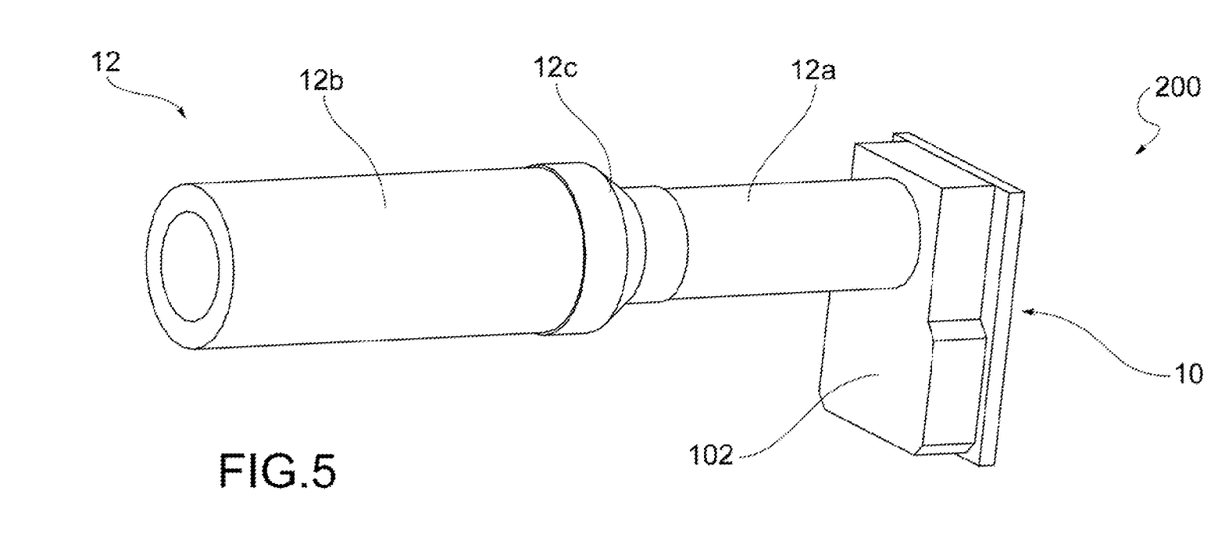
FIG. 5 is a perspective view of a detection device according to the invention, in a different embodiment, suitable in particular for abdominal surgical procedures.
Figure 6:
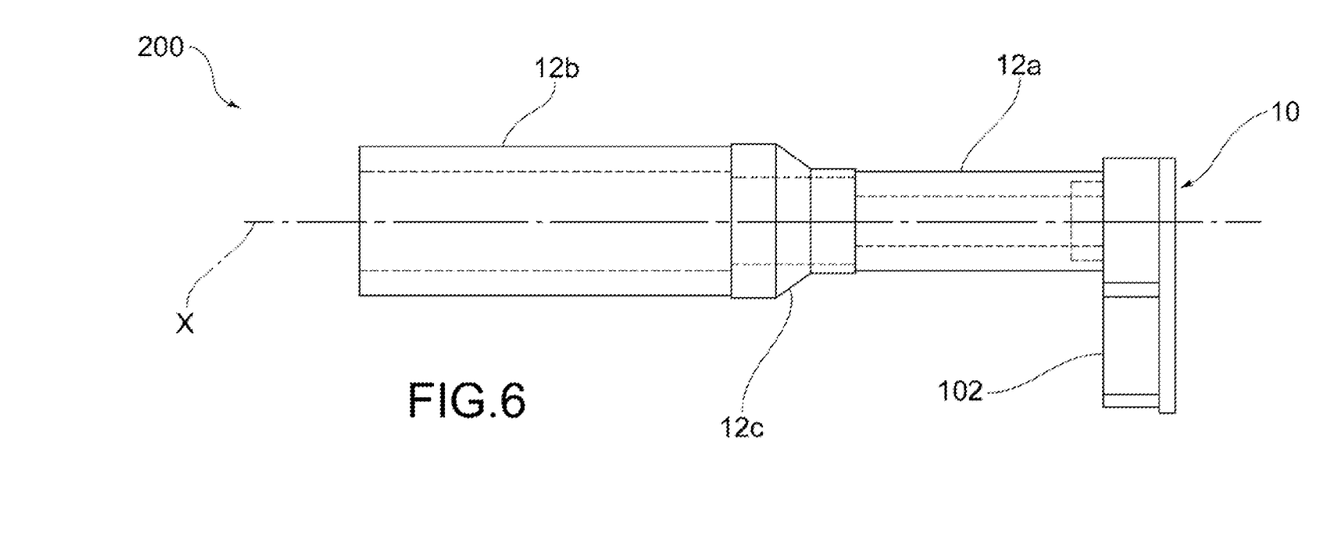
FIG. 6 is a side view of the detection device in FIG. 5.
Figure 7:
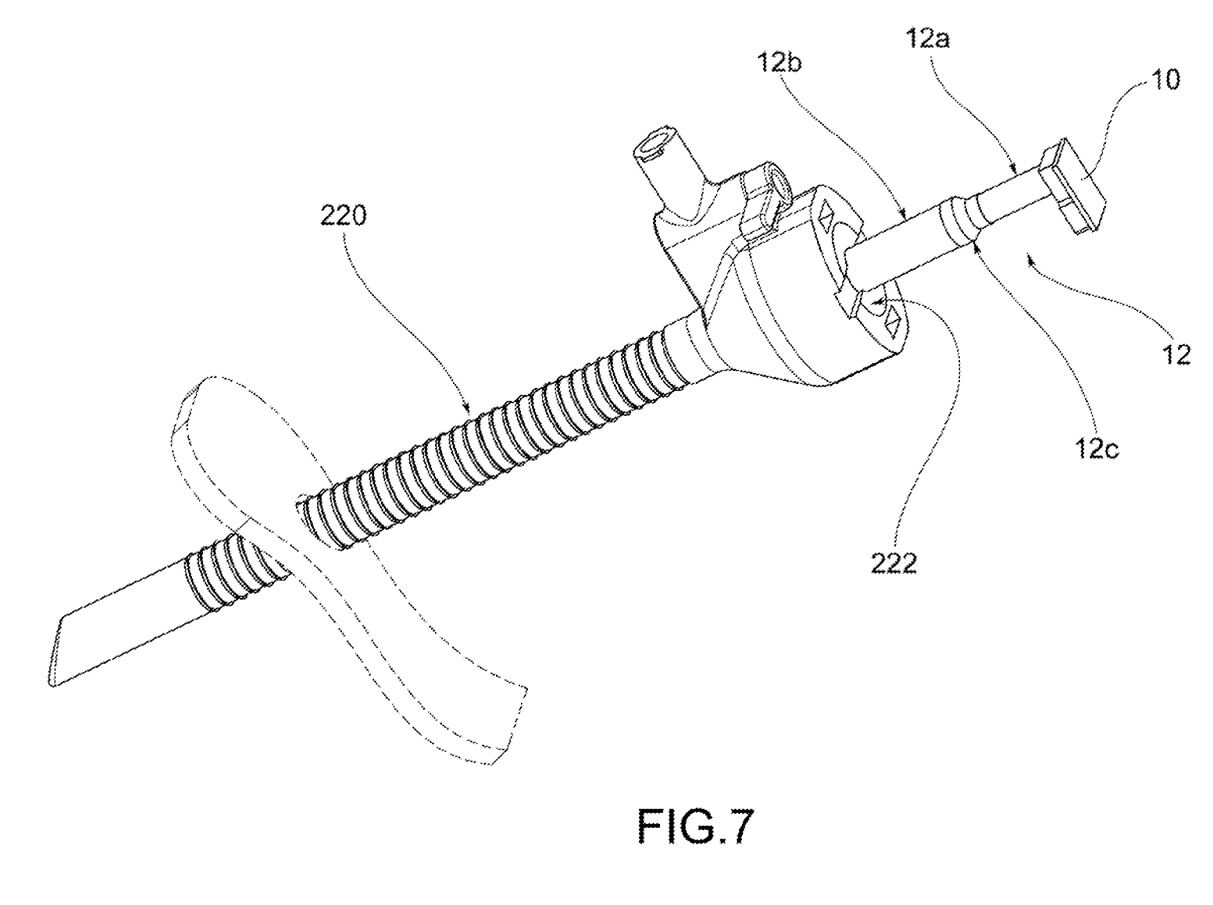
FIG. 7 is a perspective view of the detection device in FIGS. 5 and 6 coupled to the guiding cannula of a trocar.

FIGS. 5-7 show a detection device 200 in another embodiment suitable, for example, for laparoscopic surgical procedures.

The detection device 200 can use the same pressure transducer 10 described above coupled to the cannula 12.

The cannula 12, in this case, is suitable to interface directly with a guiding cannula 220 of a trocar, instead of with a needle, as illustrated in FIG. 7. The guiding cannula 220 of the trocar thus constitutes the hollow insertion means 14.

More in detail, the cannula 12 comprise a proximal portion 12a, a distal portion 12b, which is larger in diameter than the diameter of the proximal portion 12a, and an intermediate portion 12c connecting the proximal portion 12a and the distal portion 12b.

The proximal portion 12a ends with the proximal end 122 in direct contact with the sensing surface 102.

The distal portion 12b is suitable to be fluid-tightly inserted into the inlet port 222 of the guiding cannula 220.

Therefore, the distal portion 12b has a diameter corresponding to that of the inlet port 222 of the guiding cannula, the trocar for laparoscopic surgical procedures being larger than, for example, trocars for ocular or lumbar surgical procedures.

It is worth noting that in the proposed detection device, a pressure variation within the body cavity is transmitted to the pressure transducer through a single column of air (or other gas) into which any type of liquid (vitreous, saline, any preparation injected by the surgeon during the surgical procedure) can leak and mix without compromising the detected pressure measurement and in any case under electrically isolated conditions. This single column of air, formed by the cannula 12, thus effectively places the pressure transducer 10 into contact with the only access area to the body cavity through the access port formed by the hollow insertion means 14. Therefore, there is no need to thread and implant anything into the body cavity and no need to make barriers or compartments in the volume which defines the individual air column.

Furthermore, since the pressure transducer 10 and the cannula 12 are used, during the surgical procedure, completely outside the body cavity of which pressure variations are to be detected, such components of the detection device do not need to be made of materials and shapes suited for contact with the body cavity, to the advantage of simplicity and cost of production of the device.

Therefore, the detection device according to the invention can also detect a real-time pressure data, is an external and non-implantable device, being only in direct contact through an access port with to the cavity and not partitioned or compartmentalized by the cavity. For these reasons, it is applicable to minimally invasive surgery such as ophthalmic or laparoscopic surgery.

Figure 8:
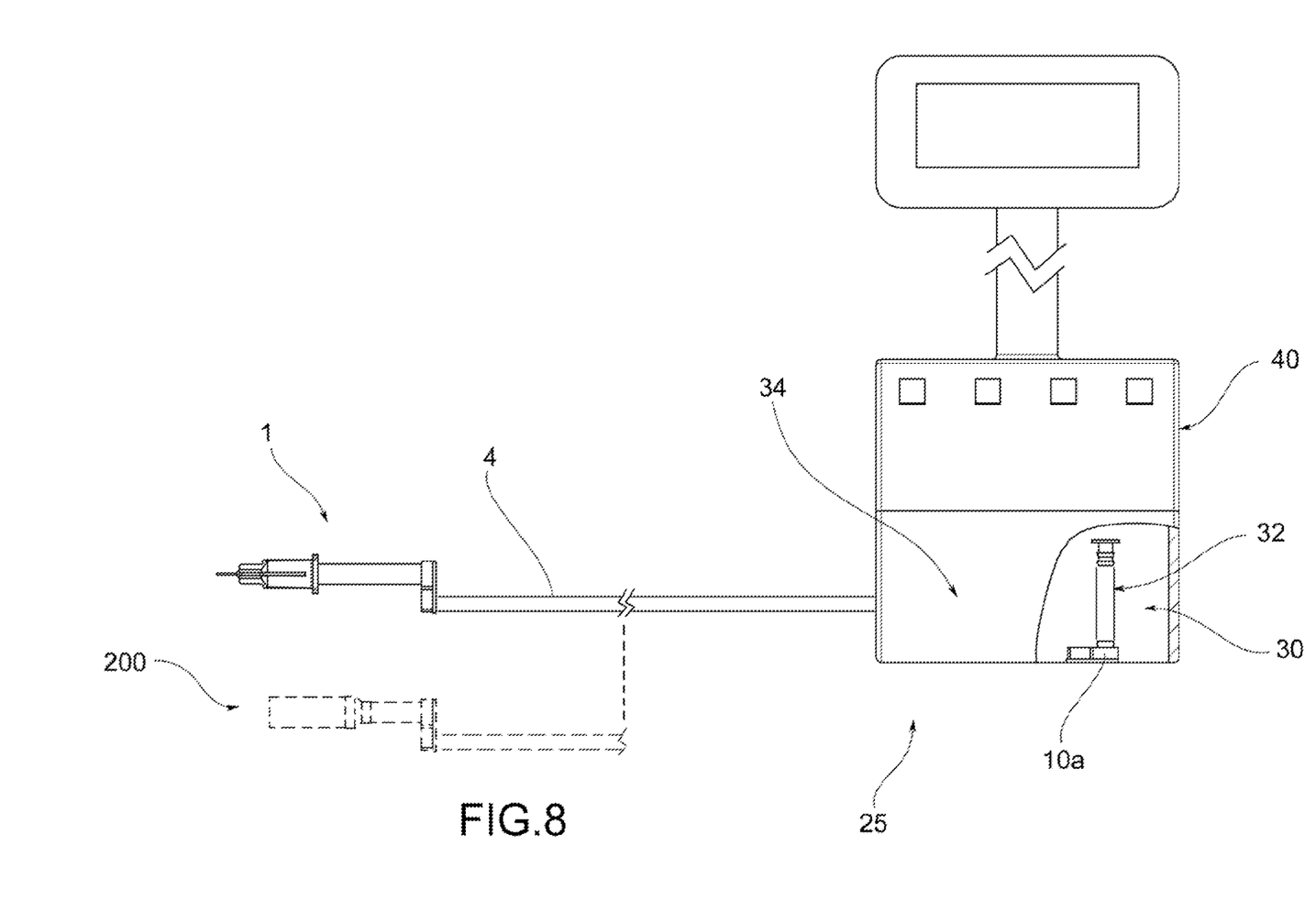
FIG. 8 is a simplified view of a detection assembly according to the invention.

It is further an object of the present invention to provide an assembly 25 for detecting pressure variations comprising a calibration system 30 of the pressure transducer 10, in addition to the detection device 1; 200 described above in its various embodiments.

The pressure transducer 10 is associated with a theoretical calibration curve, i.e., obtained in a clean room, thus in the absence of any disturbance or perturbation.

However, the pressure transducer 10 is used in the operating room, in close proximity to the patient's eye.

According to an aspect of the invention, the calibration system 30 comprises a second pressure transducer 10a which is identical to the pressure transducer of the intraocular pressure sensing device 10.

A tubular container 32 is fluid-tightly coupled to the second pressure transducer 10a.

This tubular container 32 is suitable to contain a calibration fluid, e.g. a saline solution, so that the calibration fluid applies a predetermined and invariable reference pressure on the sensing surface of the second pressure transducer 10a.

The calibration system 30 includes a control unit 34 configured to perform the steps of:

calculating a calibration curve off-set as the difference between the electrical voltage value generated by the second pressure transducer 10a at the reference pressure and the voltage value corresponding to the reference pressure in the theoretical calibration curve;

summing the calculated calibration curve offset to all values of the theoretical calibration curve.

In other words, the calibration system 30 provides an offset reference for self-calibration of the system-preloaded calibration curve of the pressure transducer 10 to be connected to the eye. Such a differential configuration, in addition to avoiding calibration procedures when opening the surgical kit, cancels stochastic noise and measurement disturbances to the benefit of the accuracy of the detection device 1; 200.

Therefore, the pressure transducers 10, 10a are calibrated in a clean room at the end of production; the second transducer 10a (subjected to a fixed pressure given by the weight of a predetermined column of the calibration fluid, e.g. a saline solution) updates the offset of the calibration curve of the first pressure transducer 10, to correct the drifts from a variation of environmental conditions between the clean room and the operating room.

For example:

offset=voltage value of the reference system at 20 mmHg–voltage value at 20 mmHg in the calibration curve.

The offset is algebraically added to all values of the calibration curve.

As shown in FIG. 8, in an embodiment, the calibration system 30 is housed in the same control apparatus 40 to which the detection device 1; 200 which measures the pressure variation is operatively connected.

A person skilled in the art can make changes and adaptations to the embodiments of the detection device, the detection assembly and the calibration method according to the invention or can replace elements with others which are functionally equivalent to satisfy contingent needs without departing from the scope of protection of the appended claims. All the features described above as belonging to one possible embodiment may be implemented independently from the other described embodiments.

The invention claimed is:

1. A device for the direct detection of pressure variations of a fluid within a body cavity during an eye surgical procedure or other minimally invasive surgical procedures, comprising:

a pressure transducer having a sensing surface suitable to deform mechanically by effect of a pressure acting on said sensor surface and generate an electrical voltage difference proportional to the mechanical deformation, a cannula having a proximal end in direct contact with the sensing surface and a distal end which either forms or is fluidically coupled with hollow insertion means suitable to be inserted into the body cavity, the cannula and the hollow insertion means forming a volume which contains an air column that can be compressed or decompressed by a pressure variation of the fluid inside the body cavity, the pressure variation of the air column being suitable to cause mechanical deformation of the sensing surface, wherein the hollow insertion means comprise a needle suitable to pierce the tissues to access the body cavity or is a guiding cannula of a trocar, and wherein the hollow insertion means is the only portion of the device configured to be inserted in the body cavity in such a way to form an access port which, in use, puts the cannula located externally to the body into communication with the inside of the body cavity.

2. A device according to claim 1, wherein the hollow insertion means comprises a blunt needle.

3. A device according to claim 1, wherein the distal end of the cannula is connected to the hollow insertion means by means of a Luer lock type connection.

4. A device according to claim 1, wherein a blunt needle is inserted into the guiding cannula.

5. A device according to claim 1, wherein the cannula comprises a proximal portion, a distal portion having a diameter greater than the diameter of the proximal portion, and an intermediate connecting portion between the proximal portion and the distal portion, the distal portion being hermetically inserted into the inlet port of a guiding cannula of a trocar, e.g. for laparoscopic surgical procedures.

6. A device for the direct detection of pressure variations of a fluid within the abdominal cavity during laparoscopic surgical procedures, comprising:
   a pressure transducer having a sensing surface suitable to deform mechanically by effect of a pressure acting on said sensor surface and generate an electrical voltage difference proportional to the mechanical deformation,
   a cannula comprising a proximal portion, a distal portion having a diameter greater than the diameter of the proximal portion, and an intermediate portion connecting the proximal portion and the distal portion, wherein the proximal portion terminates in a proximal end in direct contact with the sensing surface, and wherein the distal portion is suitable to be hermetically inserted into the inlet port of a trocar guiding cannula, wherein the trocar guiding cannula is the only portion of the device configured to be inserted in the abdominal cavity in such a way to form an access port which, in use, puts the cannula located externally to the body into communication with the inside of the abdominal cavity.

7. A device according to claim 1, wherein the pressure transducer is a piezoelectric transducer.

8. A device according to claim 7, wherein the piezoelectric transducer has a sensing surface which extends predominantly on a plane substantially orthogonal to the axis of the cannula.

9. A device according to claim 1, wherein the cannula comprises a rigid or semi-rigid tubular body to act also as a gripping element of the detection device during use.

10. A device according to claim 1, wherein the cannula is hermetically and mechanically coupled to the pressure transducer to also act as a support element for the pressure transducer.

11. An assembly for the direct detection of pressure variations in a fluid, comprising a detection device according to claim 1 and a pressure transducer calibration system, wherein the pressure transducer is associated with a theoretical calibration curve, wherein the calibration system comprises:
   a second pressure transducer identical to the pressure transducer of the intraocular pressure sensing device;
   a tubular container fluid-tightly coupled to the second pressure transducer and suitable to contain a calibration fluid, e.g. a saline solution, so that the calibration fluid applies a predetermined and invariable reference pressure on the sensing surface of the second pressure transducer;
   a control unit configured to perform the steps of:
      calculating a calibration curve offset as the difference between the electrical voltage value generated by the second pressure transducer at the reference pressure and the voltage value corresponding to the reference pressure in the theoretical calibration curve;
      summing the calculated calibration curve offset to all values of the theoretical calibration curve.

12. A method for calibrating a detection device according to claim 1, comprising the steps of:
   obtaining a theoretical calibration curve for the pressure transducer;
   making available a second pressure transducer identical to the pressure transducer of the intraocular pressure sensing device;
   fluid-tightly coupling a tubular container containing a calibration fluid, e.g. a saline solution, to the second pressure transducer so that the calibration fluid applies a predetermined and invariable reference pressure on the sensing surface of the second pressure transducer;
   calculating a calibration curve offset as the difference between the electrical voltage value generated by the second pressure transducer at the reference pressure and the voltage value corresponding to the reference pressure in the theoretical calibration curve;
   summing the calculated calibration curve offset to all values of the theoretical calibration curve.

\* \* \* \* \*